(12) United States Patent
Exner

(10) Patent No.: US 6,838,251 B1
(45) Date of Patent: Jan. 4, 2005

(54) METHOD FOR DETERMINING THE COAGULATION POTENTIAL OF A PLASMA SAMPLE

(75) Inventor: Thomas Exner, Gordon (AU)

(73) Assignee: Gradipore Limited, Frenchs Forest (AU)

(*) Notice: Subject to any disclaimer, the term of this patent is extended or adjusted under 35 U.S.C. 154(b) by 0 days.

(21) Appl. No.: 09/601,073

(22) PCT Filed: Feb. 1, 1999

(86) PCT No.: PCT/AU99/00069

§ 371 (c)(1),
(2), (4) Date: Jun. 6, 2001

(87) PCT Pub. No.: WO99/39212

PCT Pub. Date: Aug. 5, 1999

(30) Foreign Application Priority Data

Feb. 2, 1998 (AU) .............................................. PP1596

(51) Int. Cl.[7] ................................................. C12Q 1/56
(52) U.S. Cl. ........................................ 435/13; 436/69
(58) Field of Search ............................... 435/13; 436/69

(56) References Cited

U.S. PATENT DOCUMENTS

| | | | | |
|---|---|---|---|---|
| 5,601,995 A | * | 2/1997 | Exner ........................... | 435/13 |
| 5,643,739 A | * | 7/1997 | Varadi et al. .................. | 435/13 |
| 5,726,028 A | * | 3/1998 | Kraus ........................... | 435/13 |
| 5,780,255 A | * | 7/1998 | Preda ........................... | 435/23 |
| 6,051,434 A | * | 4/2000 | Exner ........................... | 436/69 |
| 6,251,619 B1 | * | 6/2001 | Van Dreden .................. | 435/13 |

FOREIGN PATENT DOCUMENTS

| | | |
|---|---|---|
| AU | 69785/87 | 9/1987 |
| DE | 3724443 | 2/1989 |
| WO | WO 91/01382 | 2/1991 |

OTHER PUBLICATIONS

Thromb, Haemost, Mar. 1997, 77(3) pp. 436–439, Armando Tripodie et al, Screening for the FV:Q506 Mutation– Evaluation of Thirteen Plasma Based Methods for their Diagnostic Efficacy in Comparison with DNA Analysis; pp. 436–437 (methods section) and p. 438 col. 2 lines 1–5.

Thrombosis Research 1997 87(6) pp. 501–510 Katharina Ruzicka et al., Evaluation of a New Screening Assay Proc® Global Identification of Defects in the Protein C/protein S Anticoagulant Pathway.

* cited by examiner

*Primary Examiner*—Ralph Gitomer
(74) *Attorney, Agent, or Firm*—Baker & McKenzie

(57) ABSTRACT

A method of determining the coagulation potential of a plasma sample be pre-incubating the plasma sample with a reagent such that endogenous protein C in the plasma is at least partially converted into activated protein C by the reagent, adding factor Xa which is progressively inactivated by antithrombin III/heparin cofactor 2 during the preincubation, adding an exogenous reagent which activates factor X to Xa or prothrombin to thrombin in a factor V-dependent manner, monitoring a reaction indicative of the rate of coagulation of the plasma sample, comparing that rate of coagulation control, or the equivalent rate determined for an individual without impaired coagulation control, or the equivalent rate determined for the plasma sample in the absence of protein C activator, and determining the coagulation potential of the plasma sample from one or other of the compairsons.

20 Claims, 5 Drawing Sheets

METHOD FOR DETERMINING THE COAGULATION POTENTIAL OF A PLASMA SAMPLE

This application is a U.S. nation stage application filed under 35 U.S.C. §371 based on international application No. PCT/AU99/00069 filed Feb. 1, 1999, which claims priority from Australian application No. PP 1596 filed Feb. 2, 1998.

TECHNICAL FIELD

The present invention relates to an improved test for measuring blood coagulation potential of patients' plasma for the purpose of predicting risk of thrombosis.

BACKGROUND ART

Mechanisms for blood coagulation, thrombosis and haemostasis are well described in International Patent Publication WO 91/01382 the contents of which are incorporated herein by reference.

It is known from International Patent Publication WO 93/01261 and publications by Bertina et al 1994 and Dahlback et al 1995 that the risk of thrombosis in patients with a mutant factor V molecule known as the Leiden variant, or with activated protein C impairment for some other reason, may be determined by activating the coagulation system in a plasma sample and incubating the sample with activated protein C in what has come to be known as an activated protein C impairment, impedance or resistance test. There are precedents for this test in which impairment of activated protein C has been detected in patents with acquired thrombophilia (Mitchell et al, 1986; Amer et al. 1988).

New tests have recently been proposed to screen for most defects in the protein C pathway (PCP) thereby to rationalise the approach to individual assays for protein C, S and factor V(Leiden) which are currently requested together in all cases of thrombophilia investigation, with a very low rate of abnormality finding. These 2-stage clotting tests usually involve activating the patient's own plasma protein C either with thrombin/thrombomodulin complex or the activator from *Agkistrodon Contortrix* venom, commonly referred to as PROTAC™ of Pentapharm, Basle. This activated protein C (APC) then inactivates the patient's own factor Va in a protein S-dependent manner during a subsequent clotting test, yielding longer clotting times than if protein C had not been activated. Clotting times shorter than normal are obtained when defects in protein C and protein S occur as well as when APC resistant factor V(Leiden) is present. Such tests have been described based oil Activated Partial Thromboplastin Times (APTT) eg AU 28416/95, EP 718628 "Method for diagnosis of blood coagulation disorders", dilute prothrombin time tests (PT) and WO 96/42018 "Thrombosis risk test".

A substrate conversion reaction rate may be determined by the coagulation time or by the time required for the conversion of a chromogenic substrate to a coloured product. The conversion rate obtained is compared with values obtained in the absence of protein C activator or PCA and also with results on normal plasma samples. If the coagulation time is not sufficiently prolonged by protein C activator, it indicates that the individual from which the sample is derived may be at a higher-than-normal risk of thrombosis.

It is well known that activation of endogenous protein C in plasma by the activator from *A. Contortrix* venom prolongs subsequent clotting times to a degree related to the protein C content. Several other factors, however, influence or interfere with this test. These factors include protein S, factor V(Leiden) which are now recognised as thrombotic risk factors in their own right.

The present inventor has recently developed an improved APC resistance test which is described in WO 96/04560. This test requires the addition of exogenous reagents which activate factor V and activate the common pathway of the blood coagulation mechanism through factor X or by inducing the formation of thrombin in a factor V dependent manner together with exogenous APC to a plasma sample. It was found that if factor V is specifically activated by an exogenous reagent in addition to activation of the common pathway through factor X, the test for APC resistance may be made more sensitive and specific than previously known tests. The present inventor has also found that improved specificity is obtained when a complex factor X activator is used together with the factor V activator. This test, because the Russells viper venom contains activators of both factor X and factor V, has been referred to as the Russells Viper Venom (RVV)-based test. A similar result is achieved if prothrombin is activated to thrombin by a factor V dependent activator in the presence of a factor V activator such as those from Australian elapid venoms.

The protein C pathway is one of a number of antithrombotic mechanisms operating within normal blood vessels to control coagulation and prevent thrombosis. Probably the most important of these mechanisms is the glycosaminoglycan (GAG) pathway which requires antithrombin III as a cofactor and heparin cofactor 2. Thrombin and factor Xa are controlled by these two plasma inhibitors which are modulated by glycosaminoglycans such as heparin sulphates normally on endothelial cells lining healthy blood vessels.

The present inventor has made the surprising finding that such tests may be further modified to allow improved discrimination between healthy individuals and patients with impaired or aberrant blood anti-thrombotic mechanisms.

DISCLOSURE OF INVENTION

In a first aspect, the present invention consists in a method of determining the coagulation potential of a plasma sample, the method comprising the steps of:

(a) preincubating the plasma sample with a reagent such that
 (i) endogenous protein C in the plasma is at least partially converted into activated protein C by the reagent, and
 (ii) adding factor Xa which is progressively inactivated by antithrombin III/heparin cofactor 2 during the preincubation;

(b) adding to the preincubated plasma sample (a) reagents to initiate clotting comprising:
 (i) an exogenous reagent which activates factor X to Xa or prothrombin to thrombin in a factor V-dependent manner, and
 (ii) components, such as phospholipid and calcium ions, that are necessary for efficient coagulation of the plasma sample;

(c) monitoring a reaction indicative of the rate of coagulation of the plasma sample;

(d) comparing the rate of coagulation detected in step (c) with the equivalent rate determined for a normal patient, or comparing the rate of coagulation detected in step (c) with the equivalent rate determined for the plasma sample in the absence of protein C activator; and (e) determining the coagulation potential of the plasma sample from one or other of the comparisons of step (d).

The reagent used in step (a) preferably also contains low levels of glycosaminoglycans such as regular or low molecular weight heparins, dermatan or dextran sulphates in addition to factor Xa The inclusion of these components to the reagent makes the test more sensitive to antithrombin III.

Preferably, the reagent used in step (a), which transforms protein C into activated protein C, is diluted substantially whole snake venom, preferably diluted snake venom from *Agkistrodon Contortrix*, or related species such as *A. Piscovorus, A. Bilineatus, A. C. Laticinctus, A. C. Moccason*. It has been found that by selecting an appropriate concentration of the snake venom, it is possible to obtain a diagnosis of impaired anticoagulation by the one test. A protein C pathway (PCP) ratio of below a pre-determined value can be indicative of impaired coagulation control in the patient's plasma. When using *A. Contortrix* whole venom diluted at a concentration of about 0.002%, it is possible to differentiate between plasma from normals, whether these come from healthy or pregnant or lupus anticoagulant positive individuals and plasma from individuals with thrombotic risk factors such as APC resistant factor V(Leiden) and protein C deficiency. A PCP ratio in this instance of below about 2 would be positive in the present test. Similarly for a concentration of 0.003%, a value of below 2.5 would be positive (see FIG. 1).

Preferably, the incubation in step (a) is carried out at neutral or slightly basic conditions, more preferably at about pH 7.5. The incubation is carried out for sufficient time for activation of the protein C in the plasma. Typically incubation times of around 5 minutes as usual for the preincubation interval in most automated APTT test methods have been found to be sufficient.

The present inventor has made the surprising finding that the protein C activator purified from *A. Contortrix* venom (a commercial product "Protac™" available from Pentapharm AB (Switzerland)) does not work very well in the present invention (see FIG. 2). The present inventor has found that dilute *A. Contortrix* venom is particularly suitable. It is possible that the purification process used to produce this commercial protein C activator removes an additional activator or agent that is present in whole venom which is preferably required for the present invention. The precise nature of the ingredient is not yet clear, however, it would appear to be a procoagulant unaffected by deficiency of vitamin K-dependent factors or Warfarin treatment. It will be appreciated that this additional activator or agent could also be purified from whole venom and combined with any commercially available purified protein C activator for use in the present invention. The individual active fractions may also be purified and recombined to produce a reagent suitable for the present invention.

Factor Xa of either human or animal origin can be included and incubated with the protein C activator reagent. This factor can be formed from endogenous factor X by venom activators Factor Xa tends to shorten clotting time. Thus the level of Russells viper venom which needs to be present ill the second reagent (with the calcium and phospholipid) to yield clotting times of 80–120 seconds on normal plasma, similar to those in regular protein C pathway tests, can be proportionally reduced. Also, heparin or glycosaminoglycans can be included in the preincubation reagent to enhance the interaction between antithrombin III and factor Xa to enhance sensitivity to low levels of antithrombin III.

In a preferred form of the present invention, the patient's plasma sample is incubated with an exogenous activator for protein C and factor X. The exogenous activator of protein C is preferably highly diluted and unfractionated *Agkistrodon contortrix* venom. The factor X activator is preferably derived from the venom of Russell viper (*Vipera Russelli*) and other immunologically cross-reactive species. The snake venoms may either be used in a diluted but unfractionated form which contributes to the simplicity of the test or, preferably, may be used in a fractionated form utilising isolated venom components.

Rather than directly activating factor X with an exogenous reagent in the second stage of such tests one may also obtain an improvement over the known activated protein C test by utilising an exogenous reagent that induces in the plasma the presence of thrombin in a factor V dependent manner. In this aspect of the invention factor V dependent prothrombin activators such as those from certain Australian *Notechis* and *Pseudonaja venoms*, such as *Pseudonaja Textilis, Notechis Scutatus* and *Oxyuranus Scutellatus*, may be used. The use of this system by-passes factor X and all factors above it thereby making the test more specific than that based on Russells viper venom alone. The use of additional venom-derived factor V activators is desirable exactly as described above for the Russell viper venom activated system which involves factor X activation.

In one embodiment of the invention, the components in step (b) with which the patient's plasma and its pre-incubants are to be mixed are combined into a single mixture. Such a single mixture preferably also contains supplemental components such as suitable buffers and preservatives. In addition the mixture preferably contains polybrene or another similar agent to reverse the effect of any heparin that may be present in the test samples or which may be added in the preincubation reagent (i). The incubation mixture preferably also contains relatively high levels of phospholipid at high ionic strength to overcome non-specific inhibitors such as lupus anticoagulants that may be present in the plasma sample.

Another complicating feature in test plasma samples may be the defect caused by oral anticoagulants. Many such thrombotic patients may already be on oral anticoagulant treatment and this affects the coagulation tests currently used to assess activated protein C resistance. The conventional method for minimising such interference is by mixing test plasma with factor V deficient plasma. The present invention, however, does not necessarily require such manipulation as such antithrombotic agents if used within their therapeutic range do not necessarily adversely effect the test. The rationale behind this is apparent from FIG. 1.

In another embodiment of the present invention, factor Xa may be used in the preincubation reagent at such a high level that no additional Russells viper venom may be required in the second mixed reagent (comprising then only phospholipid and calcium) to yield an ideal clotting time of 100 seconds with normal plasma (intended range of 50–200 seconds). In this case, the clotting time should be mainly affected by levels of autithrombin 111 (ATIII) and heparin cofactor 2 (HCF2) and not by protein C or S nor by the presence of factor V(Leiden). In this scenario, the method could be referred to as a test for the glycosaminoglycan pathway or a "GAG" test, The GAG test serves as a complimentary role to PCP tests as a preliminary screening test for likely defects in ATIII and HCF2, though in practice, it appears poorly sensitive to HCF2 (see FIG. 4). This may not be a problem, however, as HCF2 in fact is of doubtful importance as a thrombotic risk factor in comparison to ATIII.

Most tests for ATIII and HCF2 presently used require a preliminary high dilution of the test plasma to be carried out. This is usually in a buffer containing high levels of heparin or GAGs to facilitate complete interaction of thrombin or factor Xa with ATIII or HCF2. The quantitative loss in thrombin or factor Xa enzyme activities is then converted to functional ATIII or HCF2 present in the test plasma. However, if a single thrombophilia screening test proves to be sensitive enough to all the known thrombotic risk factors in diagnostic practice, then an appropriate mixture of ACCV/PCA and factor Xa in the preincubation reagent and dilute Russells viper venom/phospholipid/recalcifying reagent to provide equal sensitivity to all the known thrombotic risk factors would be preferred.

The detection system for monitoring the potential rates of change within the coagulation system may be a coagulation time assay or a chromometric or fluorometric assay using an appropriate synthetic substrate. Such detection systems are well known and described in the patent specifications referred to in the introductory portions of this specification.

Some patients' plasma may give borderline results when assayed by the method according to the present invention such that it is not possible to determine unequivocally between "normal" and factor V(Leiden) deficient plasma samples. The present inventor has made the surprising discovery that diluting these "borderline" samples with low ionic strength solutions including water and carrying out the method according to the first aspect of the present invention can differentiate between normal and factor V(Leiden) samples. The method according to the first aspect of the present invention also provides improved discrimination of FVL heterozygotes from homozygous individuals.

In a second aspect, the present invention consists in method to differentiate between patients with factor V(Leiden) from normal individuals, the method comprising diluting plasma from the patients and the normal individuals with low ionic strength solutions including water and repeating the method according to the first aspect of the present invention.

Preferably, the plasma are diluted 1:1 with water, preferably distilled or filtered water, prior to repeating the coagulation assay. The factor V(Leiden) plasma will usually have ratios equal to or less than the ratios obtained when undiluted. Furthermore, the ratios obtained for the factor V(Leiden) plasma will usually be less than the ratios obtained for normal plasma assayed with the same test conditions. Prior to the present invention, it would have been necessary to add factor V deficient plasma to all plasma test samples and then re-assay for clotting abnormalities.

The use of low ionic strength solutions, and particularly distilled water, is significantly cheaper than factor V deficient plasma that is required in tests currently used. Furthermore, low ionic strength solutions, and particularly distilled water, are far easier to source than factor V deficient plasma. The present invention therefore offers a real advantage in cost and tests requiring factor V deficient plasma presently in In a third aspect, the present invention consists in a method of testing antithrombin III deficiency in a plasma sample, the method comprising the steps of:

(a) preincubating a first sample of a test plasma with factor Xa:

(b) adding to the preincubated first test plasma a reagent to initiate clotting and measuring the clotting time of the preincubated test plasma;

(c) adding to a second sample of the test plasma a reagent to initiate clotting and measuring the clotting time of the second test sample; and (d) comparing the clotting times of the first and second test samples, wherein a shorter clotting time in the first test sample being indicative of antithrombin III deficiency in the plasma sample.

Preferably, in step (a) the first test plasma is preincubated with an equal volume of factor Xa in buffer for around 5 minutes at 37 degC. More preferably, ill step (a) test plasma (0.1 ml) is preincubated with an equal volume of factor Xa (optimally 0.002 u/ml or higher if GAGs are added) in 0.02 M HEPES buffer at pH 7.2 for 5 minutes at 37 degC.

Preferably in step (b) a further equal volume of calcium chloride containing soybean lecithin is added to initiate clotting of the preincubated sample and the time to clot is determined. More preferably in step (b) a further equal volume (0.1 ml) of 0.02 M calcium chloride containing 0.1% soybean lecithin is added to initiate clotting of the preincubated sample. A target range of about 80–120 sec has been found for normals.

The above result is compared with that obtained when the same test plasma is clotted with of a mixture of the two reagents (ie. the FXa reagent and the calcium chloride/phospholipid reagent). Preferably the same test plasma (0.1 ml) is clotted with 0.2 ml of a 1:1 mixture of the 2 reagents (ie. the FXa reagent and the calcium chloride/phospholipid reagent). A target range of about 30–35 sec has been found for normals.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

In order that the nature of the present invention may be more clearly understood, a preferred form will be described with reference to the following example and the accompanying drawings.

MODES FOR CARRYING OUT THE INVENTION

Method

Figure 1:
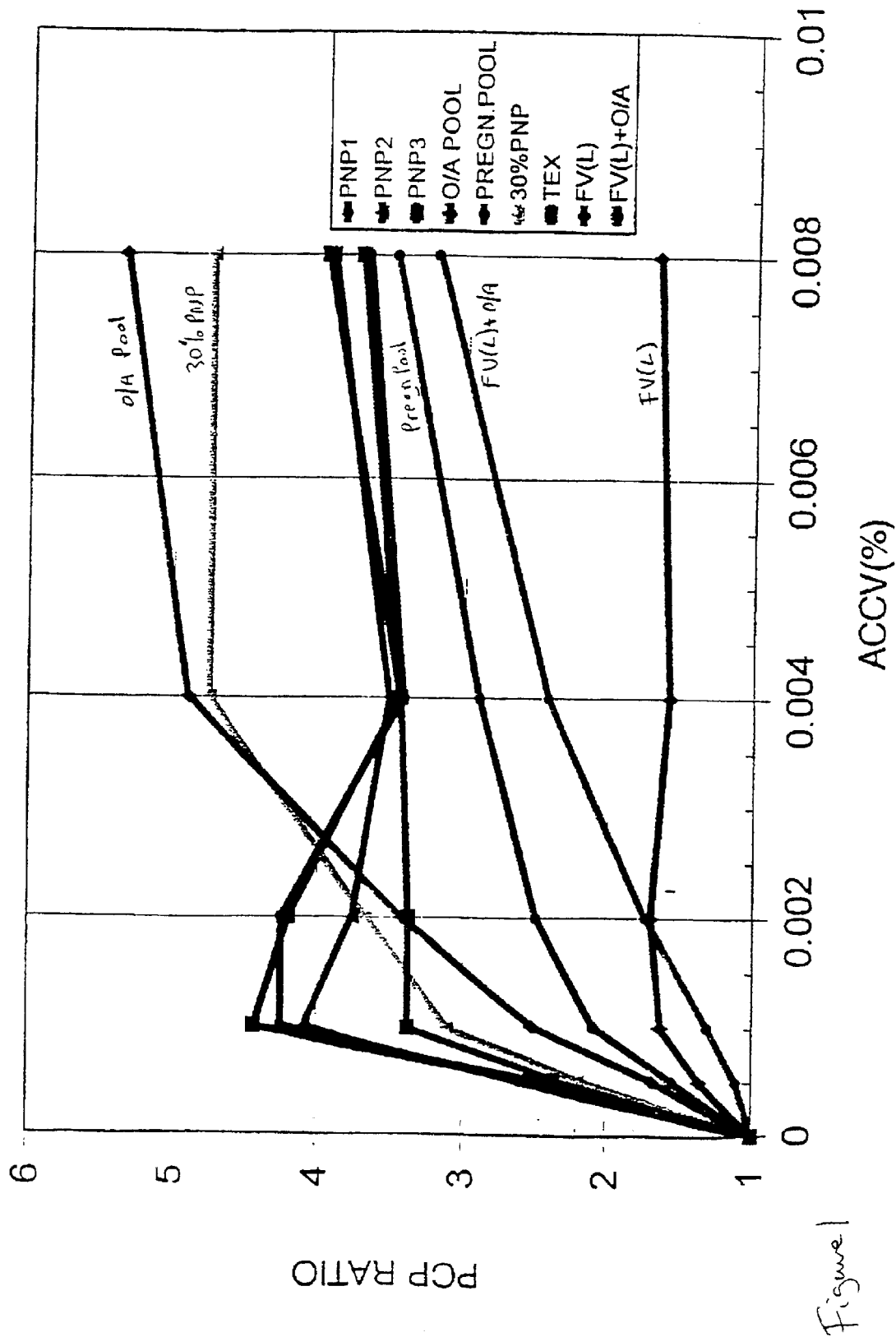
FIG. 1 shows effect of varying ACCV level in PCP/FVL tests on various test plasmas. Test plasmas preincubated for 5 minutes with varying levels of ACCV and then clotted with RVV/phospholipid/calcium reagent (LA-Confirm) in ACL300 in APFT mode. Showing RVV clotting time ratios (PCP ratios) plotted against the concentration of ACCV (%).
Figure 2:
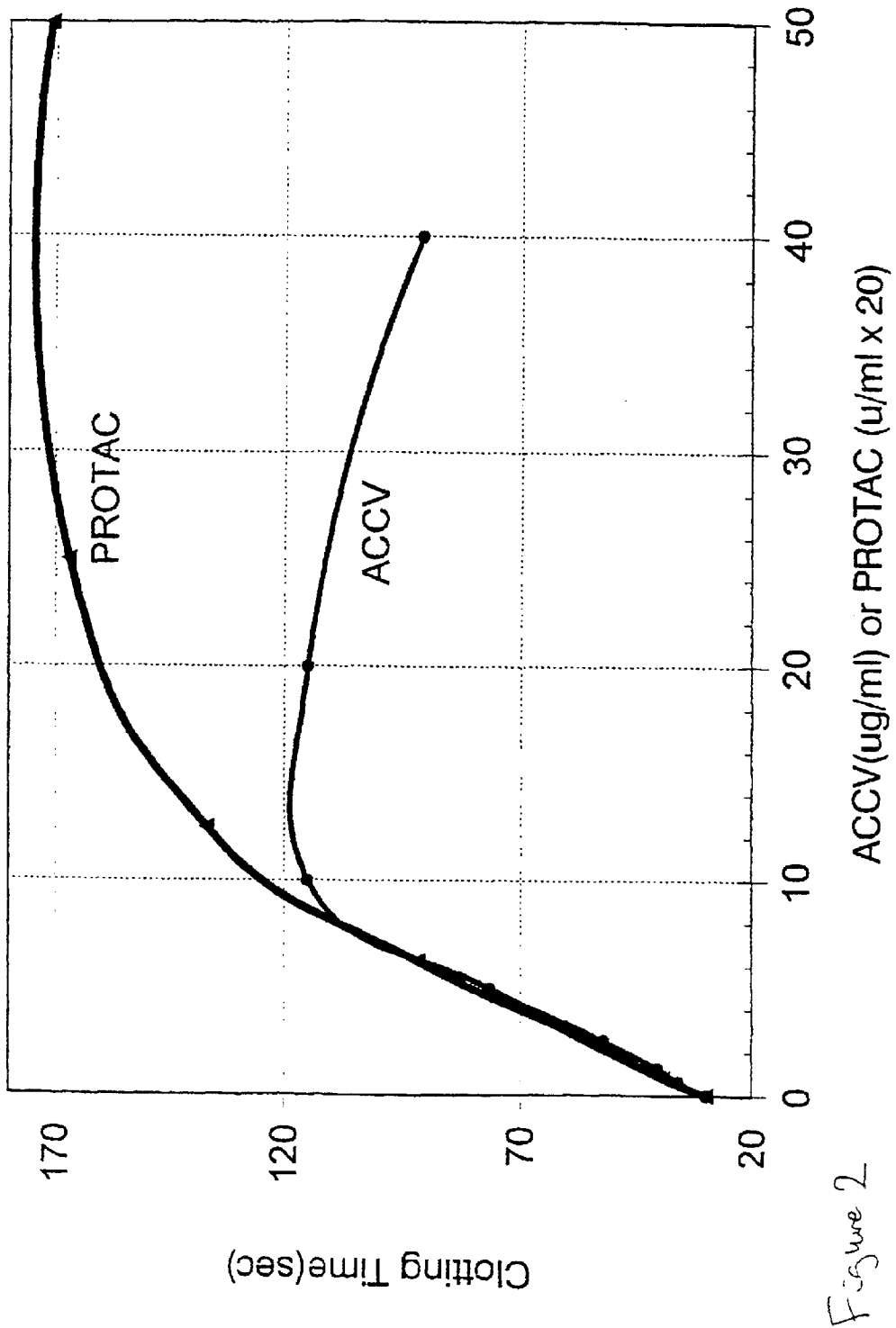
FIG. 2 shows Protac™ or whole dilute *Agkistrodon Contortrix C.* venom (ACCV) dilutions were preincubated with pooled normal plasma for 5 minutes and then clotted with phospholipid-rich Russells viper venom reagent (LA-Confirm). Results show the RVV clotting times obtained on an ACL300 clotting machine plotted against the concentration of Protac™ (u/ml/20) or ACCV(ug/ml) used. (Note that PCP ratios are calculated as the RVV clotting times with any given ACCV or Protac™level divided by the clotting time with no activator present).
Figure 3:
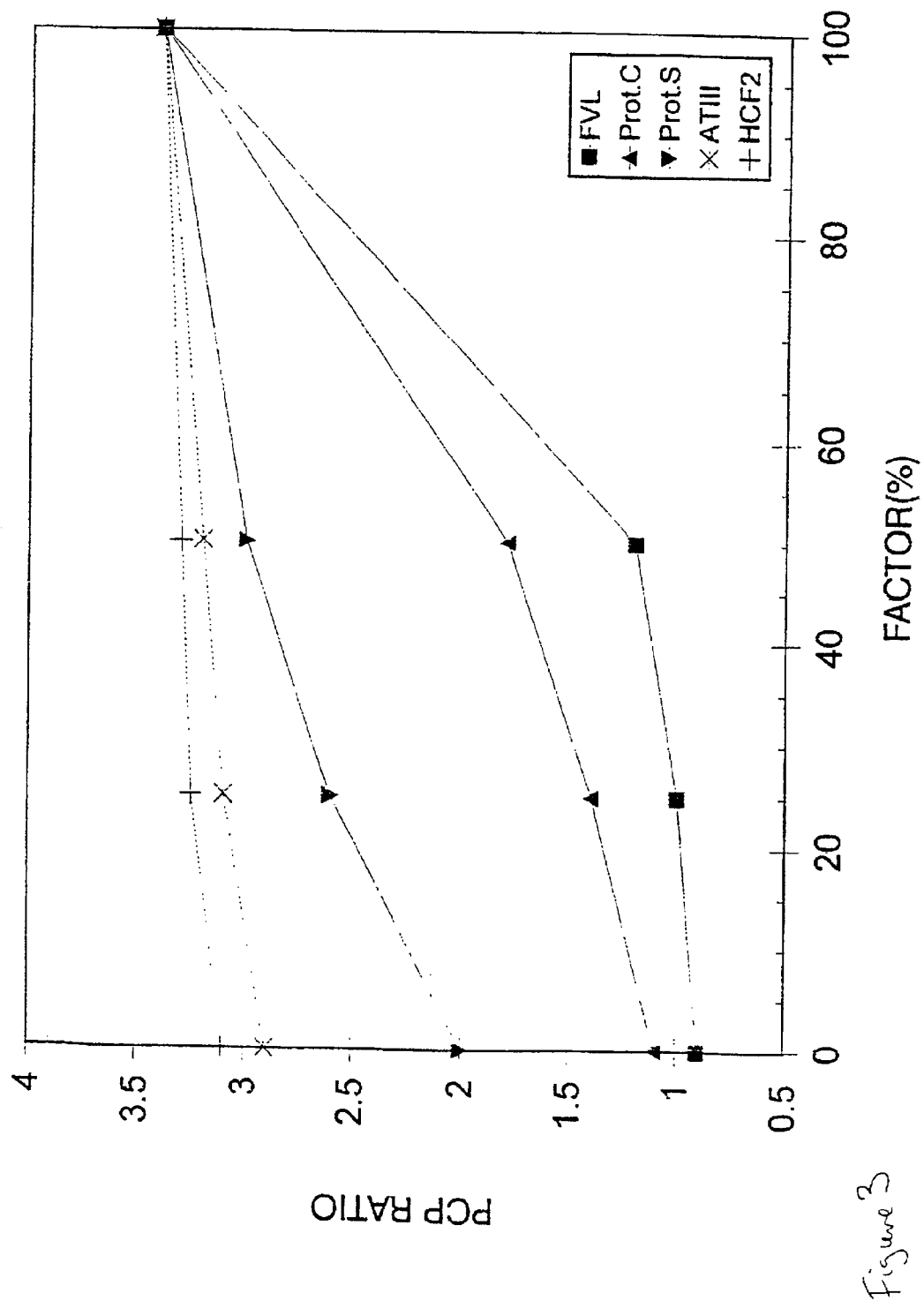
FIG. 3 shows effect of individual thrombotic risk factors on the PCP carried out with dilute whole ACC venom. Showing PCP ratios (RVV clotting times with and without protein C activation) plotted against level of each factor shown. From top to bottom; HCF2; ATIII; Prot.S, Prot.C, Factor V(Leiden). Mixes prepared from individual factor deficient or factor V(Leiden) positive (heterozygote) plasmas and pooled normal plasma, itself representing 100%.
Figure 4:
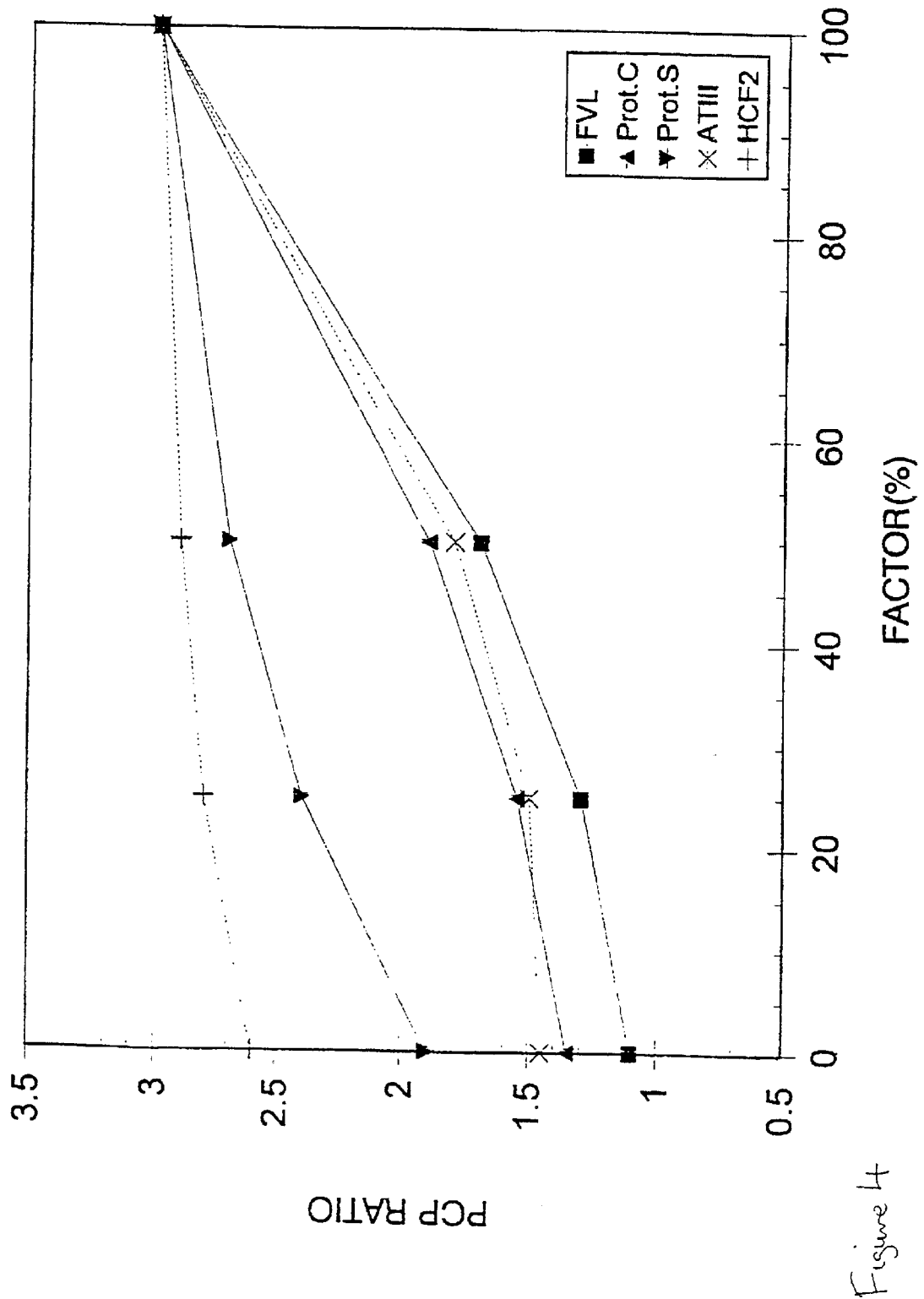
FIG. 4 shows effect of individual thrombotic risk factors on a mixed GAG/PCP test system. Preincubation reagent contained dilute whole ACCV and 0.002 u/ml factor Xa. Reagent was mixed with each test plasma for 5 minutes at 37 degC before being clotted with a reduced Russells viper venom reagent/phospholipid/calcium reagent. Results show the ratios of clotting times with and without preincubation plotted against factor level. In descending order on left axis; HCF2, Prot.S, ATIII, Prot.C, Factor V(Leiden).
Figure 5:
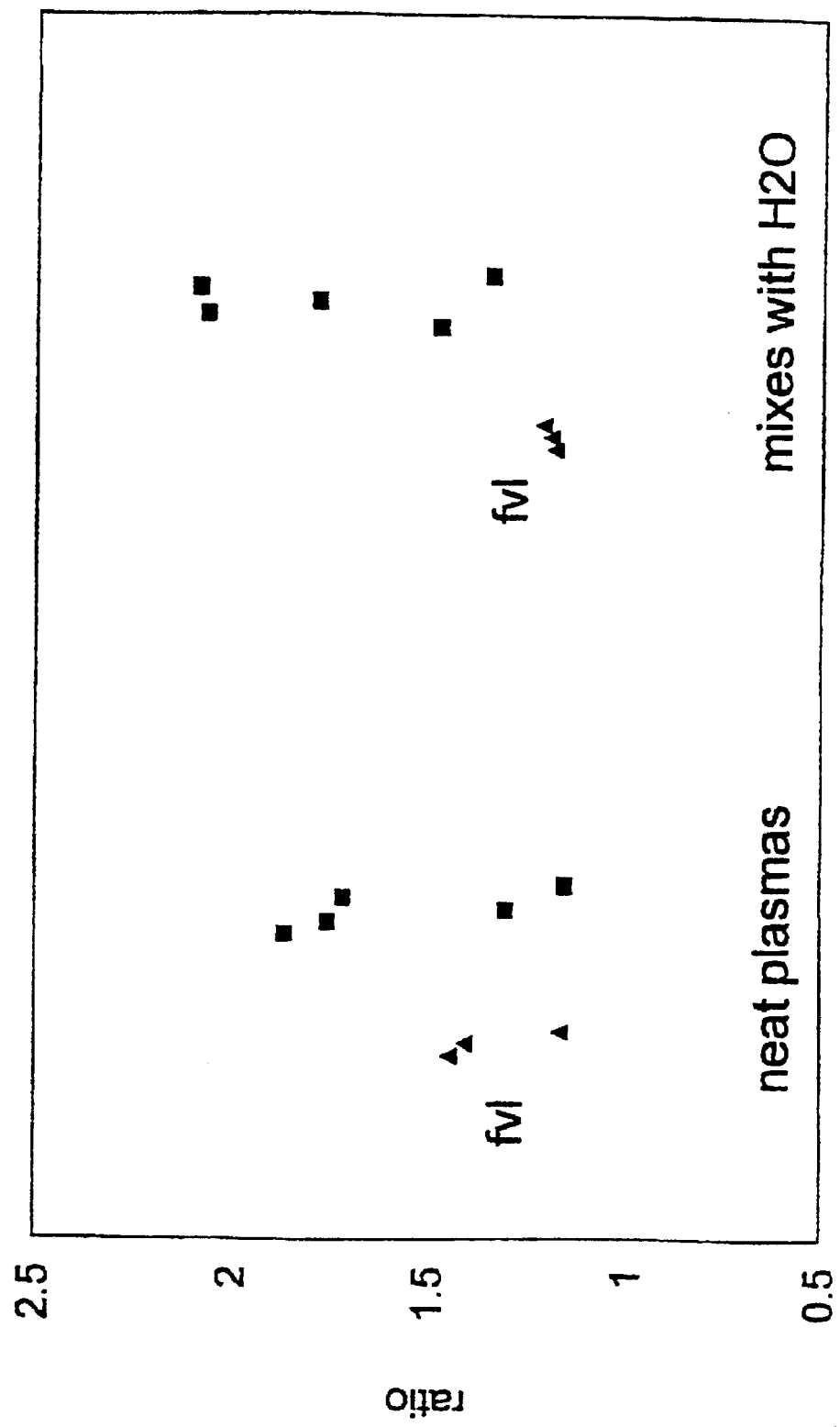
FIG. 5 shows borderline PCP/FVL results. Results show scatterplot of PCP/FVL ratios obtained on selected several warfarin patient with neat and water-diluted plasmas. Eight (8) neat plasmas all gave borderline abnormal ratios (1.2–1.8), but after dilution with water, improved discrimination of FVL cases from normals was achieved.

A method is described for a clotting test which is more specific for detecting resistance to activated protein C due to the factor V(Leiden) mutation than the original system described by Dahlback. The method involves 2 steps. In the first step, test plasma is incubated with dilute whole *Agkistrodon Contortrix* venom at 0.002–0.004% and pH 7.5 for 5 minutes. In the second step, phospholipid-rich Russell viper venom is added and the time required for a fibrin clot to form is determined.

A "control" or blank test to detect baseline coagulation abnormalities may be carried out in exactly the same way, except that no *Agkistrodon Contortrix* venom should be present in the first pre-incubation step. Chromogenic substrates could be used as an alternative to clot formation for detecting the formation of thrombin, but these are more expensive.

Mechanism

It is known that *Agkistrodon Contortrix* venom contains an activator of protein C. The active component has been isolated and sold under the trade mark "Protac™" by Pentapharm AB (Switzerland). Protac™ has been patented for use in tests for quantitating protein C and more recently in tests for assessing the function of the protein C pathway (PCP) as described above. During the course of the first incubation (above) protein C in the test plasma is converted to an enzymatically-active form (activated protein C or APC). This is a powerful anticoagulant which destroys factors Va and VIIIa, thereby interfering with the clotting mechanism and prolonging certain clotting tests. In individuals who are deficient in protein C or S, the anticoagulant effect of the venom protein C activator is reduced relative to normal and the clotting times are shorter than normal. Also, if the patient plasma contains a commonly-occurring mutation in factor V called the FV(Leiden) variant, the clotting times are less prolonged by either activated protein C or the venom protein C activator than with normal plasma. FV(Leiden) lacks a specific APC sensitive cleavage site involved in the inactivation of normal factor V and therefore it persists in such test systems and shortens the clotting times.

All of these defects interfere with the normal functioning of the PCP and are associated with clinical thrombosis. All three defects are usually detectable by a shorter than normal clotting test result in the presence of protein C activator. Patients who are on oral anticoagulants have reduced levels of vitamin K-dependent clotting factors as well as protein C and S and cannot usually be screened for factor V(Leideni) which such a test. It has become conventional to mix such patient's plasma with factor V deficient plasma to "correct" all clotting factor defects and protein C and S levels prior to carrying out an APC resistance tests for factor V(Leideni).

The present iwventor has found that use of whole diluteA-glistrodoii CoiitortrLY venom (ACCV) is preferable to the use of isolated protein C activator in the RVV-based PCP test described in WO 96/04560 for the following reasons. The test becomes insensitive to protein S deficiency (which is a less important thrombotic risk facto than FVL or protein C) and less affected by low protein C levels and more sensitive to factor V(Leiden). The effect of relatively high levels of ACCV on the RVVT of normal plasma seems to be similar to that of lower levels, unlike that of the isolated activator which prolongs the RVVT to an increasing degree with concentration. Higher levels of ACCV can be used to activate the small concentrations of protein C found in patients on oral anticoagulants for more effect in the test and to overcome acquired APC resistance in patients taking oral contraceptives or who are pregnant. Thus by using higher levels of the whole ACCV it is possible to screen for the Factor V(Leiden) defect in plasma from Warfarin patients, pregnancy plasma and other conditions which previously required mixing with factor V deficient or other normalising factors.

Advantages

1. No need to mix test plasma with factor V deficient plasma for the detection of factor V(Leiden) among complex patients.

2. Plateau concentration dependencies means higher levels of ACCV can be added with a less prolonged normal clotting time.

Method

The improved test is based on the factor V(Leiden)-specific PCP screening test which uses a phospholipid-rich RVV reagent. The composition of the reagent has been modified to make it less sensitive than usual to variations in Protein C and Protein S levels in the presence of a protein C activator. Since this RVV reagent is already designed to be heparin and lupus anticoagulant resistant and since its mechanism is through the common pathway, this test is more reliable than those based on APTTs and PTs.

Reagents

1. Protein C Activator (PCA)

Preparation

Reconstitute in volume of distilled water as indicated on the vial

Gently invert to mix- DO NOT shake

Allow to stand at room temperature for 10 minutes before use.

2. PRVV Reagent (Phospholipid-rich Russell viper venom reagent)

Preparation

Reconstitute in volume of water as indicated on the vial

Gently invert to mix- DO NOT shake

Allow to stand at room temperature for 10 minutes before use.

Reconstituted Stability

| Product | Conditions | Time |
| --- | --- | --- |
| PCA | 2–8° C. | 48 hours |
|  | 37° C. | 12 hours |
| PRVV | 2–8° C. | 48 hours |
|  | 37° C. | 12 hours |
|  | −20° C. (freeze thaw only once) | 1 month |

Specimen

Mix nine parts of freshly collected blood with one part 3.5% (0.12 M) trisodium citrate. Centrifuge as soon as possible after collection at >1500 g for 15 minutes. Separate plasma and store at 2–8° C. Test within 4 hours of collection. Plasma may be stored frozen at −30° C. or below for up to six months.

Jaundiced, lipaemic and haemolysed specimens can give false clotting time results. These results may also occur in patients with abnormal haematocrits, as plasma to citrate concentration in these samples is not optimal.

Test Procedure

Method

The PCP Test is not affected by Heparin levels of up to 0.5 IU/ml.

Test with PC Activator
1. Pre-warm a slight excess of PRVV reagent, allowing 0.1 ml per test, to 37° C.+1° C. in a reagent reservoir.
2. Dispense 0.1 ml of test plasma into a test tube.
3. Add 0.1 ml of Activator to the test plasma and warm at 370° C. for 5 minutes.
4. Add 0.1 ml pre-warmed PRVV reagent and time from the moment of addition of the reagent to a clotting end-point using the tilt tube technique.
5. Repeat for duplicate test values and report the average of these as the result.

Test without PC Activator
1. Pre-warm a slight excess of PRVV Reagent, allowing 0.1 ml per test, to 37° C.+1° C. in a reagent reservoir.
2. Dispense 0.1 ml of test plasma into a test tube.
3. Add 0.1 ml of distilled water to the test plasma and warm at 37° C. for 5 minutes.
3. Add 0.1 ml pre-warmed PRVV Reagent and time from the moment of addition of the reagent to a clotting end-point using the tilt tube technique.
5. Repeat for duplicate test values and report the average of these as the result.

The results of PCP tests of varying *A. Contortrix* whole venom levels on various test plasma are shown in FIG. 1. The use of levels of between 0.002 to 0.004% ACCV in the test allows the differentiation between sera from normal individuals (PNP1, PNP2 and PNP3), oral anticoagulant pool (O/A pool) and pooled sera from pregnant individuals (PREG.POOL), from patients with impaired clotting function (FV(L) and FV(L)+O/A). PCP values of below 2 and 2.5, respectively for tests using 0.002 and 0.004% ACCV are seen to be indicative of impaired clotting.

FIG. 1 shows the protein C pathway (PCP) clotting time ratios (clotting times with protein C activator present/those without activator) obtained on a series of patients and normals using increasing levels of *Agkistrodon Contortrix Contortrix Venom* (ACCV). Normal plasmas show the largest effect initially, but seen to dip down at ACCV levels above 0.002%. Oral anticoagulant-treated, factor deficient (partially alumina adsorbed) and pregnancy plasmas show a more gradual increase with no evidence for a dip. Factor V(Leiden) positive plasmas all remain low. Thus, by selecting an appropriate ACCV level of approximately 0.003% it is possible accomodate all the FVL negative cases within a tight PCP ratio range, representing the normal or reference range, regardless of several other complicating factors. (Note that this RVV-based system is already insensitive to therapeutic levels of heparin and to any abnormalities involving factors above factor X in the clotting pathway.)

FIG. 2 shows a direct comparison of Protac™ with *Agkistrodon Contortrix* venom (ACCV) in the PCP test. Increasing levels of both protein C activators were added to pooled normal plasma prior to testing with the phospholipid-rich dilute RVV reagent. Both activators resulted in similarly prolonged clotting times at levels below 10 ug/ml for ACCV or 0.5 u/ml for Protac. However, above this concentration the Protac™ gave further prolongation, whereas the ACCV gave shorter clotting times. This is the reason for the unexpected "dips in the PCP ratios for normal plasma in FIG. 1 at ACCV levels above 0.002%. It is this PCP ratio "dip" with normals which allows valid comparisons against similar measurements of APC resistance and PCP defects on plasmas with defects such as those due to oral anticoagulants as shown in FIG. 1.

Factor V(Leiden) Confirmation Assay

In order to differentiate between normal and factor V(Leiden) samples which gave "borderline" results in the blood clotting assay according to the present invention, samples were re-assayed after first being diluted 1:1 in distilled water. The results are shown in FIG. 5. The three factor V(Leiden) samples tested produced lower ratios than those of the normal samples re-assayed after dilution with water. This finding allows the testing of samples without the need to add factor V deficient plasma to the samples to be assayed.

GAG test

This basic test is carried out in two parts: Firstly, a two stage procedure involving a preincubation, like an APTT and second, a one step test without preincubations, just like a PT test.

In the 2 stage procedure, test plasma (eg 0.1 ml) is preincubated with an equal volume of factor Xa (optimally 0.002 u/ml or higher if GAGs are added) in 0.02 M HEPES buffer at pH 7.2 for 5 minutes at 37 degC. Then a further equal volume(0.1 ml) of 0.02 M calcium chloride containing 0.1% soybean lecithin is added and the time to clot is determined. The target range is 80–120 sec for normals.

The above result is compared with that obtained when the same test plasma (0.1 ml) is clotted with 0.2 ml of a 1:1 mixture of the 2 reagents (ie. the FXa reagent and the calcium chloride/phospholipid reagent). The target range is 30–35 sec.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

BERITNA RM, KEULEMANS BPC, KOSTER T, et al.- Mutation in blood coagulation factor V associated with resistance to activated protein C. Nature 369; 64–67, 1994.

DAHLBACK B - Inherited Thrombophilia: Resistance to activated protein C as a pathogenic factor of venous thromboembolism. Blood 85; 607–614, 1995

MITCHELL CA, ROWELL JA, HAU L, et al.- Fatal thrombotic disorder associated with an acquired inhibitor of protein C. N. England J. Med. 317; 1638–16, 1987

AMER L, KISIEL W, SEARLES RP, WILLIAMS JRC - Impairment of the protein C anticoagulant pathway in a patient with systemic lupus erythematosus, anticardiolipin antibodies and thrombosis. Thromb. Res. 57, 247–1990

What is claimed is:

1. A method of determining the coagulation potential of a plasma sample, the method comprising the steps of:

(a) pre-incubating the plasma sample with a reagent such that (i) endogenous protein C in the plasma is at least partially converted into activated protein C by the reagent, and (ii) adding factor Xa which is progressively inactivated by antithrombin III/heparin cofactor 2 during the preincubation;

(b) adding an exogenous reagent which activates factor X to Xa or prothrombin to thrombin in a factor V-dependent manner to the preincubated plasma sample of step (a);

(c) monitoring a reaction indicative of the rate of coagulation of the plasma sample;

(d) comparing the rate of coagulation monitored in step (c) with the equivalent rate determined for an individual without impaired coagulation control, or comparing the rate of coagulation detected in step (c) with the equivalent rate determined for the plasma sample in the absence of protein C activator; and (e) determining the coagulation potential of the plasma sample from one or other of the comparisons of step (d).

2. The method according to claim 1 wherein the reagent of step (a) further contains low concentrations of glycosaminoglycans.

3. The method according to claim 2 wherein the glycosaminoglycans are selected from the group consisting of regular or low weight heparins, and dermatan or dextran sulphates.

4. The method according to claim 1 whereby the exogenous agent that transforms protein C into activated protein C is substantially diluted whole snake venom.

5. The method according to claim 4 whereby the snake venom is *Agkistrodon* species including *Agkistrodon Contortrix*, or a related species including *A. Piscovorus, A. Bilineatus, A. C Laticinctus*, and *A. C. Moccason*.

6. The method according to claim 5 wherein the venom is *A. Contortrix* whole venom and diluted at a concentration of about 0.002%.

7. The method according to claim 5 wherein the snake venom is diluted *A. Contortrix* whole venom.

8. The method according to claim 1 wherein the preincubation in step (a) is carried out at neutral or slightly basic conditions.

9. The method according to claim 8 wherein the preincubation step is carried out at pH 7.5.

10. The method according to claim 1 whereby the preincubation is carried out for sufficient time for activation of protein C in the plasma.

11. The method according to claim 10 wherein the preincubation time is about 5 minutes.

12. The method according to claim 1 whereby the factor Xa is of human or animal origin.

13. The method according to claim 1 whereby the exogenous reagent which activates factor X to Xa is derived from the venom of *Russells Viper* (*Vipera Russelli*) or other immunologically cross-reactive snake species.

14. The method according to claim 1 wherein the exogenous reagent which activates prothrombin to thrombin in a factor V-dependent manner is derived from *Australian Notechis*, or *Pseudonaja* or *Oxyuranus snake venoms*.

15. The method according to claim 14 wherein the snake venom is obtained from the species selected from the group consisting of *Pseudonaja Textilis, Notechis Scutatus*, and *Oxyuranus Scutellatus*.

16. The method according to claim 1 whereby reagents in step (b) are combined with other components into a single mixture by the use of surfactants.

17. The method according to claim 16 wherein the surfactants are non-ionic detergents.

18. The method according to claim 16 or 17 wherein the single mixture further contains supplemental components selected from the group consisting of buffers, preservatives, hexadimethrine bromide (polybrene) or other agents to reverse the effect of any heparin that may be present in the test samples or which may be added in the preincubation reagent (i), and phospholipid at high ionic strength to overcome non-specific inhibitors such as lupus anticoagulants that may be present in the plasma sample.

19. The method according to claim 1 whereby the monitoring a reaction indicative of the rate of coagulation of the plasma sample is a coagulation time assay or a chromometric or uorometric assay using a detectable substrate.

20. The method according to claim 1 wherein phospholipid and calcium ions are added; to the pre-incubated plasma sample.

* * * * *